United States Patent [19]

Cricchio

[11] 4,144,234

[45] Mar. 13, 1979

[54] PREPARATION OF RIFAMYCIN P AND Q DERIVATIVES

[75] Inventor: Renato Cricchio, Varese, Italy

[73] Assignee: Gruppo Lepetit S.p.A., Milan, Italy

[21] Appl. No.: 796,290

[22] Filed: May 12, 1977

[30] Foreign Application Priority Data

May 28, 1976 [GB] United Kingdom ............... 22206/76

[51] Int. Cl.² .......................................... C07D 513/18
[52] U.S. Cl. ........................... 260/239.3 P; 424/270; 424/244
[58] Field of Search ................................ 260/239.3 P

[56] References Cited

U.S. PATENT DOCUMENTS 4,042,683   8/1977   White ................................... 424/117

FOREIGN PATENT DOCUMENTS 832921   12/1975   Belgium ........................... 260/239.3 P
2537902   3/1976   Fed. Rep. of Germany .... 260/239.3 P
482716   1/1970   Switzerland ..................... 260/239.3 P

*Primary Examiner*—Henry R. Jiles
*Assistant Examiner*—Robert T. Bond
*Attorney, Agent, or Firm*—James W. Ambrosius

[57] ABSTRACT

A method for preparing thiazolorifamycin derivatives from rifamycin S and a cysteine ester to produce an intermediate product which is cyclized to thiazolorifamycin and the novel products formed therefrom.

10 Claims, No Drawings

PREPARATION OF RIFAMYCIN P AND Q DERIVATIVES

SUMMARY OF THE INVENTION

The present invention refers to a chemical process for the preparation of thiazolorifamycin derivatives of the formula:

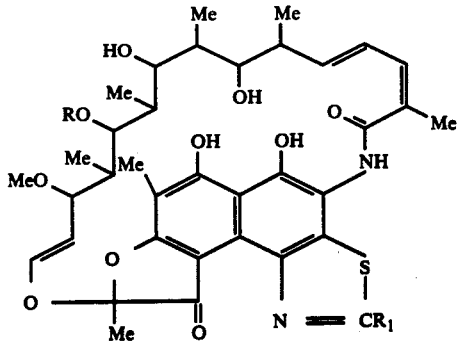

wherein R is hydrogen or $CH_3CO-$ and $R_1$ is hydrogen or $-CH_2OH$. The two compounds of formula I wherein R is $CH_3CO$ and $R_1$ is hydrogen and $-CH_2OH$ correspond to the natural products defined in Belgian Patent No. 832,921 as rifamycin P and rifamycin Q, respectively. These two microbiologically active metabolites were obtained, together with other natural products, by fermenting strains of *Norcardia mediterranei* identified with the following A.T.C.C. numbers: 31064, 31065, 31066. The chemical process of this invention offers the advantage of a more convenient route for preparing rifamycin P and Q in terms of yields, costs and purity of the products. The two compounds of formula I wherein R is hydrogen, i.e., the 25-deacetyl derivatives of rifamycin P and rifamycin Q, are novel antibacterial substances and are considered to be part of this invention.

The chemical process for preparing the compound of formula I involves the reaction of rifamycin S of the formula:

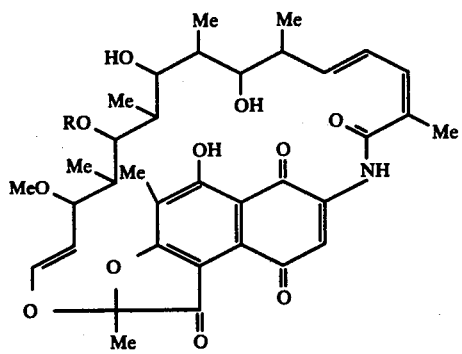

wherein R is H or $CH_3CO$ with a cysteine ester of the formula:

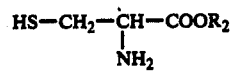

wherein $R_2$ is alkyl, cycloalkyl, phenyl or benzyl or an acid addition salt thereof such as, for example, hydrohalide or sulfate and the like. The term "alkyl" as used in the specification and in the claims identifies a straight or branched aliphatic radical of from 1 to about 8 carbon atoms. The term "cycloalkyl" identifies a 5 to 8 membered cycloalkyl ring which may optionally bear one or two lower alkyl substituents. In the desription and in the claims the terms "phenyl" and "benzyl" represent unsubstituted phenyl and benzyl groups as well as phenyl and benzyl moieties substituted with one or two groups selected from the group consisting of chloro, bromo, fluoro, nitro, lower alkoxy, cyano, trifluoromethyl, sulfamoyl and lower alkyl sulfonyl.

The following scheme wherein $R_1$ and $R_2$ have the same meanings as before summarizes the reaction pathway of the novel chemical process.

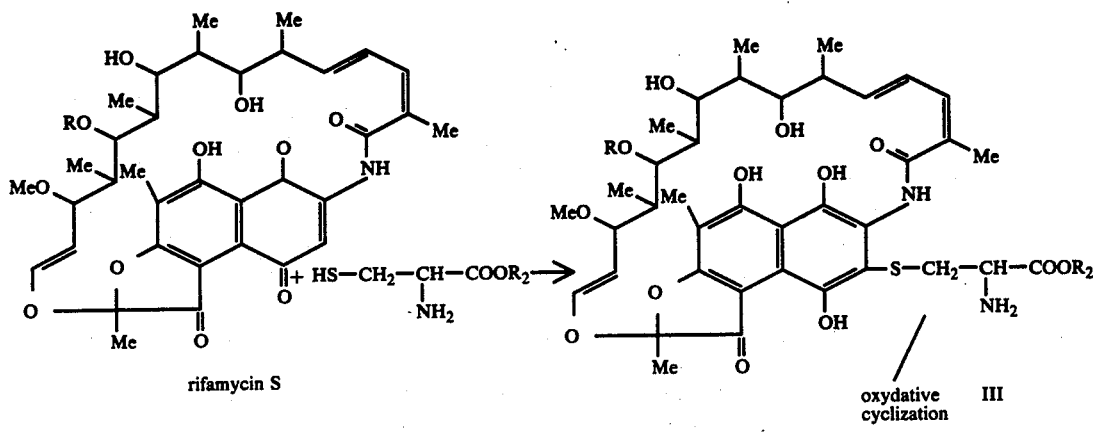

-continued

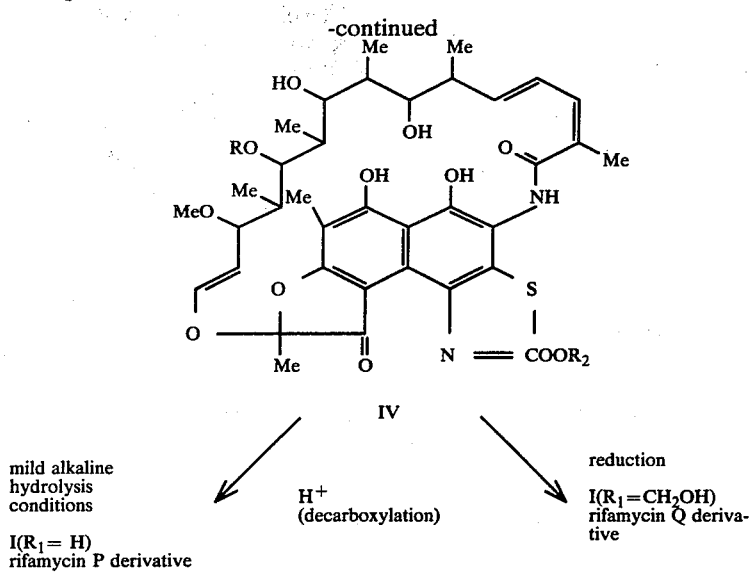

mild alkaline hydrolysis conditions
I(R₁ = H) rifamycin P derivative

H⁺ (decarboxylation)

reduction
I(R₁=CH₂OH) rifamycin Q derivative

The compounds of formula I wherein R is hydrogen may be obtained directly through the process outlined above or alternatively by the hydrolysis in a strong alkaline medium of the compounds of formula I wherein R is CH₃CO.

The reaction leading to the thiazolorifamycin intermediate of formula IV may be carried out directly, i.e., without isolating the intermediate III, or alternately the intermediate may be isolated prior to oxydative cyclization. When the reaction is carried out by isolating the intermediate III, the oxidizing agent necessary for promoting the oxidative cyclization is added to the reaction mixture after the reaction of the cysteine derivative with the rifamycin S partner is completed. The first step is carried out by contacting about equimolecular proportions of the two reactants in an organic solvent miscible with water such as, for example, lower alkanol, dioxane or tetrahydrofuran and the like. The temperature of the reaction may range between room temperature and the boiling temperature of the reaction mixture. The time required to complete the reaction depends on the temperature of the reaction, and is generally determined by observing the disappearance of rifamycin S by thin layer chromatography. The 3-(2-substituted ethylthio)-rifamycin SV intermediate (III) thus obtained is then contacted with an oxidizing agent to promote the second reaction step. Said oxidizing agent may be selected from a wide group of substances including, for example, quinones, organic nitrites, peroxides, persulfates, nitrous acid, tetravalent manganese and lead derivatives, trivalent iron derivatives, mercuric and cupric salts and the like. Among the preferred oxidizing agents are p-quinone, 2,5-dimethyl-p-quinone, 2,6-dimethoxy-p-quinone, tetrachloro-p-quinone(chloranil), dichlorodicyano-p-quinone, duroquinone, rifamycin S, alkyl nitrites, hydrogen peroxide, alkali metal persulfates, alkali metal ferricyanides, cupric acetate, mercuric acetate and manganese dioxide.

After the first stage is completed the oxidizing agent is added to the reaction mixture while the pH is maintained between 2 and 6.5, preferably between 4 and 5 and most preferably between 4.2 and 4.8, during the further reaction course. A suitable way for controlling the pH is by using an aqueous buffer. This second step of the reaction which is defined as "oxidative cyclization" is advantageously carried out at a temperature between room temperature and the boiling temperature of the reaction mixture. The preferred temperature range for the reaction is between about 18° C. and about 45° C. The reaction course is generally followed by thin layer chromatography (eluent chloroform-methanol 9:1) since formation of the thiazolorifamycin IV is easily detected as a fluorescent yellow spot with an Rf value of about 0.4. When the reaction is completed the mixture is worked up in order to eliminate the oxidizing agent or its reaction products. The procedure followed generally depends on the type of oxidizer employed. Filtration and extraction operations known to the art are generally involved; in particular, when quinones are used as the oxidants it may be useful to eliminate the resulting hydroquinone derivative by reoxidizing it to the original quinone while simultaneously extracting the quinone with a proper solvent. Once the reaction side-products have been eliminated, the thiazoloroifamycin IV may be easily recovered as a crystalline product using techniques well known in the art.

The reaction leading to the intermediate IV may be carried out directly if an oxidizing agent is employed which does not unfavorably interfere with the two other reaction partners. Oxidizers which are suitable for this purpose include, for example, rifamycin S itself or a tetra-substituted quinone such as duroquinone, chloranil or dichlorodicyano-p-quinone. When the process is carried out without isolating the intermediate III about equimolecular proportions of rifamycin S substrate and of the cysteine ester reactant are dissolved in an organic solvent miscible with water such as for example, lower alkanol, dioxane and tetrahydrofuran or the like in the presence of at least a stoichiometric amount of a properly selected oxidizer. The mixture is allowed to stand at a temperature between about 18° C. and about 45° C. in the presence of an aqueous buffer system at a pH value of between 2 and 6.5, preferably between 4 and 5 and most preferably between 4.2 and 4.8. The reaction course is followed by thin layer chromatography which shows disappearance of the starting rifamycin S derivative and presence of the new yellow fluorescent spot due to the thiazolorifamycin IV. In general, after a period of time ranging from about 10 and 80 hours the reaction is completed and the mixture is worked up for separation from the side products and recovery of the thiazolorifamycin as mentioned above.

The thiazolorifamycin ester of formula IV obtained according to the procedures described above may be decarboxylated using mild alkaline hydrolysis followed by acidification to obtain the compound of formula I wherein $R_1$ is hydrogen. Suitable hydrolytic conditions are obtained with diluted alkali hydroxides or alkali carbonates.

According to one preferred embodiment of the invention the intermediate IV is dissolved in a mixture of an organic solvent miscible with water and 10 percent aqueous sodium carbonate and allowed to stand at room temperature for about 2 to 6 hours. Acidification with a strong mineral acid, extraction with a water immiscible solvent and concentration of the organic extract gives the compound of formula I mentioned above. The compound of formula I having R equal to $CH_3CO-$ has been found to be identical structurally with a sample of rifamycin P obtained through fermentation according to Belgian Patent No. 832,921. Identity has been confirmed using physico-chemical characteristics such as melting point, chromatographic behavior in different solvent systems, elemental analysis, mass spectrum, nuclear magnetic resonance spectrum, I.R., U.V. and visible light absorption spectra and also by means of microbiological tests.

The intermediate thiazolorifamycin of formula IV having a carboxyester group on the thiazole ring may be reduced with an alkali metal aluminum hydride to the corresponding derivative having a hydroxymethyl group in the same position. For this reduction step a suitable reducing agent known to have an identical effect on the carboxyester moiety is employed. Agents which may be employed include for example, $AlH_3$, $LiAlH(OCH_3)_3$, $NaBH_4$ excess, $[(CH_3)_2-CH-CH_2-]_2AlH$, $NaAl(OCH_2-CH_2OCH_3)_2H_2$, $NaB(OCH_3)_3H$ and $CaCl_2/NaBH_4$. The reaction product, i.e., a compound of formula I wherein $R_1$ is $-CH_2OH$ is easily isolated from the reaction mixture after thin layer chromatography monitoring reveals the disappearance of the starting thiazolorifamycin. The recovery procedure is carried out according to techniques known in the art which involve dilution of the reaction mixture with water and extraction with a water immiscible solvent followed by evaporation of the extract to a small volume. The product thus obtained, i.e, where R is equal to $CH_3CO-$, has been found to be identical in structure with a sample of rifamycin Q obtained through fermentation carried out according to Belgian Patent No. 832,921. Identity has been confirmed on the basis of physico-chemical characteristics such as, melting point, chromatographic behavior in different solvent systems, elemental analysis, mass spectrum, nuclear magnetic resonance spectrum, I.R., U.V. and visible light absorption spectra.

As already indicated before the compounds having R equal to $CH_3CO-$ may be easily transformed to the corresponding deacetylated derivatives by strong alkaline hydrolysis. Suitable hydrolytic conditions may be obtained by using aqueous 10 percent or more concentrated alkali metal hydroxides or alkali metal alkoxides and hydrides. These hydrolytic conditions may be employed during the decarboxylation or during the reduction step to give to the 25-deacetyl compounds of formula I directly.

The compounds obtained through the process herein described, are useful as antibacterials. In particular, they possess significant antibacterial activity in vitro and in vivo against Gram positive and Gram negative microorganisms such as, for example, *Staphylococcus aureus, Streptococcus haemolyticus, Streptococcus faecalis, Diplococcus pneumoniae, Proteus vulgaris* and *Mycobacterium tuberculosis.*

25-Deacetyl rifamycin P is a novel compound whose in vitro antimicrobial activity is as follows:

|  | Minimal inhibitory concentration ($\mu$g/ml) |
| --- | --- |
| *Staphylococcus aureus* | 0.025 |
| *Staphylococcus aureus* Tour | 0.1 |
| *Staphylococcus aureus* Tour + 30% bovine serum | 0.05 |
| *Streptococcus haemolyticus* | 0.1 |
| *Streptococcus faecalis* | 0.4 |
| *Diplococcus pneumoniae* | 0.1 |
| *Proteus vulgaris* | 0.78 |
| *Escherichia coli* | 6.25 |
| *Klebsiella pneumoniae* | 12.5 |
| *Pseudomonas aeruginosa* | 12.5 |
| *Mycobacterium tubercolosis* $H_{37}R_V$ | 0.62 |

PREFERRED EMBODIMENTS OF THE INVENTION

The following examples will serve to further illustrate the invention but are not to be construed as a limitation thereon.

EXAMPLE 1

Preparation of Rifamycin P (I; R=$CH_3CO$, $R_1$=H)

To a solution of 7 g of rifamycin S (0.01 m) in 300 ml of methanol and 20 ml of a buffer pH 4.6 (aqueous solution of citric acid and $Na_2HPO_4.12\ H_2O$) are added 0.850 g (0.005 m) of cysteine methyl ester hydrochloride. The resulting solution was left at room temperature for 72 hours at which time thin layer chromatography ($CHCl_3:CH_3OH$ 9:1 as the eluent) showed the starting rifamycin S had disappeared and the presence of a new spot with a Rf value of about 0.4 due to the presence of rifamycin SV with an Rf of 0.05 including trace amounts of various by-products. The reaction mixture was diluted with 1 liter of water and then extracted with 500 ml of ethyl acetate. A solution of 6 g of potassium ferricyanide in 500 ml of buffer pH = 7.38 was added to the organic phase, and the mixture was stirred for a few minutes to oxidize the rifamycin SV to rifamycin S which in turn is extracted by ethyl acetate. The combined buffered solutions were acidified with 10 percent HCl and then extracted with ethyl acetate. The organic phase was separated, washed with water, anydrified and concentrated under vacuum to a small volume. The product crystallized out and, after chilling, was collected on a filter and dried (2.4 g). This compound corresponds to the thiazolorifamycin of formula IV wherein R is $CH_3CO-$ and $R_2$ is $-CH_3$. The compound was found to have the following characteristics:

Melting Point: 190–205° C. (with decomposition).

| U.V. and visible absorption bands (buffer pH = 7.38) | |
| --- | --- |
| $\lambda$ max | $E_{1\ cm}^{1\%}$ |
| 225 | 573 |
| 295 | 364 |
| 394 | 238 |

Two grams of the compounds obtained according to the above described procedure were dissolved in a mixture of 150 ml of acetone and 100 ml of 10 percent aqueous sodium carbonate and left at room temperature for 4 hours with stirring.

The solution was acidified with 10 percent HCl and extracted with ethyl acetate. The organic phase was separated, washed with water, dried with $Na_2SO_4$ and concentrated to a small volume. The rifamycin P crystallized out. Yield 1.7 g. The product had the following characteristics:

Melting point: The compound melts above 190° C. with decomposition.

| Elemental analysis (%): | C | H | N | S |
|---|---|---|---|---|
| Calculated for $C_{38}H_{46}N_2O_{11}S$: | 61.77 | 6.27 | 3.79 | 4.34 |
| found: | 60.27 | 6.35 | 3.68 | 4.19 |

U.V. and visible absorption bands:
The compound shows the following values:

| methanol | | 0.1N HCl | |
|---|---|---|---|
| λ max (mμ) | $E^{1\%}_{1\,cm}$ | λ max (mμ) | $E^{1\%}_{1\,cm}$ |
| 408 | 176 | 416 | 175 |
| 350 | (shoulder) | 303 | 292 |
| 300 | 314 | 231 | 450 |
| 268 | 349 | | |
| 228 | 424 | | |

Infrared spectrum

The most significant absorption peaks in Nujol occur at the following frequencies ($cm^{-1}$): 3700–3200(m,br); 3120–3080(w); 3000–2850(vs); 1465(s); 1380(b):Nujol; 1725(m); 1640(m,br); 1580(m); 1520(m); 1325(m); 1250(s,br); 1155(m); 1130(w); 1070(m,br), 1045(w); 975(m); 950(m); 920(w); 880(m); 805(w); 760(w); 730(w).

The identity with rifamycin P obtained by fermentation is also confirmed by the chromatographic behavior in different systems and by mass and nuclear magnetic resonance spectrometry.

EXAMPLE 2

Preparation of Rifamycin P

To a solution of 7 g of rifamycin S in 300 ml of methanol was added a mixture containing 1.8 g of the hydrochloride of cysteine methyl ester and 1.53 ml of triethylamine. The resulting mixture was refluxed for 20 minutes then, after cooling, was poured into water. After acidification the aqueous mixture was extracted with ethyl acetate and the extract was evaporated to dryness yielding 6 g of 3-(2-amino-2-carbomethoxy-ethylthio)-rifamycin SV having a melting point above 160° C. with decomposition. The compound has the following characteristics:

| Elemental analysis: | C | H | N | S |
|---|---|---|---|---|
| Calculated for $C_{41}H_{54}N_2O_{14}S$: | 59.26 | 6.55 | 3.37 | 3.86 |
| found: | 57.38 | 6.51 | 3.22 | 3.65 |

U.V. and visible absorption bands (buffer 7.38):

| λ max | $E^{1\%}_{1\,cm}$ |
|---|---|
| 227 | 455 |
| 318 | 260 |
| 454 | 160 |

8.30 Milligrams of the product described above was dissolved in 30 ml of methanol and 2 ml of a buffer pH 4.6 (aqueous solution of citric acid and $Na_2HPO_4.12\,H_2O$). Dichlorodicyano-p-quinone (230 mg) were added to the mixture. After 15 hours at room temperature the reaction mixture was evaporated and the residue taken up with chloroform. The organic phase was extracted with an aqueous buffer pH 8.04. The aqueous buffer after separation from the chloroform phase was acidified and extracted with ethyl acetate. By concentrating the ethyl acetate solution the thiazolorifamycin intermediate of formula IV ($R=CH_3CO$, $R_2=CH_3$) crystallized out. Yield 200 mg. This product was transformed into rifamycin P by following the procedure described in Example 1 above.

The reaction may also be carried out by employing one of the following oxidizing agents instead of 2,3-dichloro-5,6-dicyano-p-quinone: tetrachloro-p-quinone, manganese dioxide, 2,5-dimethyl-p-quinone, 2,6-dimethoxy-p-quinone, tetramethyl-p-quinone, p-quinone.

EXAMPLE 3

Preparation of Rifamycin P

To a solution of 7 g of rifamycin S in 200 ml of methanol a mixture was added containing 1.8 g of the hydrochloride of cysteine methyl ester and 1.53 g of triethylamine. The mixture was refluxed for 20 minutes and then 20 ml of a buffer pH 4.6 containing 2.2 g of dichlorodicyano-p-quinone was added. The mixture was allowed to stand at room temperature for 15 hours and then was treated as described in Example 1 to obtain the rifamycin P. Yield 2.8 g of the title product.

EXAMPLE 4

Preparation of Rifamycin Q
(I;$R=CH_3CO$,$R_1=CH_2OH$)

To a stirred suspension of 0.5 g of $LiAlH_4$ in 10 ml of tetrahydrofuran a solution containing 1 g of the intermediate of formula IV ($R=CH_3CO$; $R_2=CH_3$) in 25 ml of tetrahydrofuran was added at room temperature. After 10 minutes, thin layer chromatography (eluent: $CHCl_3$:$CH_3OH$ 9:1) showed the disappearance of the starting rifamycin and the presence of a new spot with Rf=0.4. The reaction mixture was diluted with water, acidified with 10 percent HCl and extracted with ethyl acetate.

The organic phase was separated, washed with water, dried using $Na_2SO_4$ and concentrated to a small volume: Rifamycin Q crystallized out (0.700 g). The compound also may be prepared by employing 1 g of $NaBH_4$ instead of 0.5 g of $LiAlH_4$. The product has the following characteristics:

Melting Point: The compound melts at 178°–180° C. with decomposition.

| Elemental analysis (%) | C | H | N | S |
|---|---|---|---|---|
| Calculated for $C_{39}H_{48}N_2O_{12}S$ | 60.92 | 6.29 | 3.64 | 4.17 |
| found: | 60.69 | 6.26 | 3.60 | 4.16 |

U.V. and visible absorption bands:
The compound shows the following values (methanol):

| λ max | $E^{1\%}_{1\,cm}$ |
|---|---|
| 410 | 176 |
| 350 | (shoulder) |
| 300 | 332 |
| 260 | 384 |
| 225 | 536 |

Infrared Spectrum

The most significant absorption peaks in Nujol occur at the following frequencies ($cm^{-1}$): 3700–3100(s,br); 3030–2800(vs); 1460(s); 1375(s); Nujol; 1720(m); 1650(s,br); 1580(s,br); 1515(m,br); 1320(w); 1260(m); 1240(m); 1155(m); 1090(m); 1065(m,br); 1020(w); 970(w); 950(m); 910(m); 805(m); 765(w); 725(w).

The identity with rifamycin Q obtained by fermentation was also confirmed by the chromatographic behavior in different systems and by mass and nuclear magnetic resonance spectrometry.

EXAMPLE 5

Preparation of 25-Desacetyl-rifamycin P (I;R=H, R₁=H)

To a solution of 750 mg of rifamycin P in a mixture containing 40 ml of acetone and 10 ml of water was added with stirring 20 ml of 10 percent sodium hydroxide at 0°–5°C. The mixture was maintained for 24 hours at room temperature and then is poured into ice water acidified to about pH 2 with diluted HCl and then extracted with ethyl acetate. The organic extract was concentrated to dryness, dissolved in chloroform and then purified by column chromatography through silicagel (eluent CHCl₃ with increasing ratios of CH₃OH up to 3 percent).

The combined unitary fractions were evaporated to dryness and then the residual product after dissolution in ethyl acetate was precipitated by the addition of petroleum ether. Yield 400 mg. The product had the following characteristics:

Melting Point: The compound melts at 172°–4° C. with decomposition.

| Elemental analysis: | C | H | N | S |
|---|---|---|---|---|
| Calculated for $C_{36}H_{44}N_2O_{10}S$ | 62.05 | 6.36 | 4.02 | 4.60 |
| found: | 61.98 | 6.32 | 4.04 | 4.56 |

The U.V. spectrum is practically identical with that of rifamycin P.

By operating in the same way as described above but using rifamycin Q as the starting material, 25-desacetyl rifamycin Q is obtained as the end product.

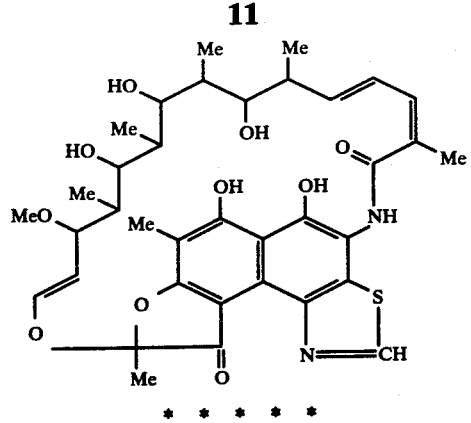

We claim:

1. A process for preparing a thiazolorifamycin of the formula:

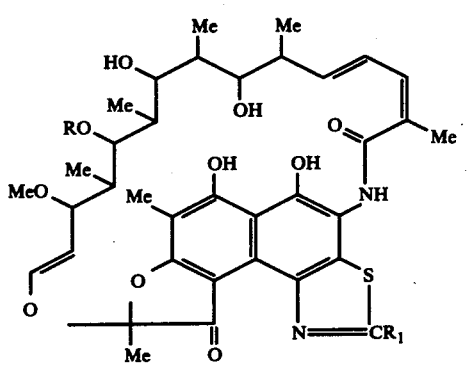

wherein R is hydrogen or CH₃—CO— and R₁ is hydrogen or CH₂OH which comprises reacting rifamycin S or its 25-desacetyl derivative in a water miscible organic solvent at a temperature between room temperature and the boiling point of the reaction mixture with a cysteine ester of the formula:

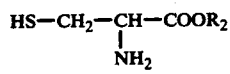

wherein R₂ represents alkyl of from 1 to about 8 carbons, 5 to 8 membered cycloalkyl, phenyl or benzyl and further including the acid addition salts thereof, whereby a 3-(2-substituted ethylthio)-rifamycin SV derivative of the formula:

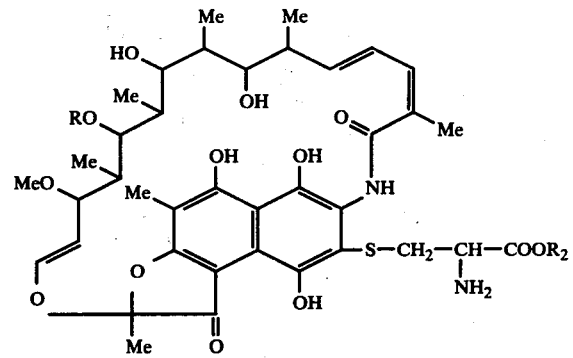

is obtained, wherein R and R₂ have the same meanings as before, contacting said derivative with an oxidizing agent in an aqueous buffered water-miscible solvent system at a controlled pH value of between 2 and 6.5, submitting the thus obtained thiazolorifamycin carboxyester to decarboxylation by using mild alkaline hydrolysis followed by acidification, or reducing its carboxyester moiety to hydroxymethyl using a suitable reducing agent.

2. A process as in claim 1 wherein the controlled pH value is between 4.2 and 4.8.

3. A process as in claim 1 wherein the solvent is selected from a lower alkanol, dioxane and tetrahydrofuran.

4. A process as in claim 1 wherein the oxidizing agent is selected from the group consisting of p-quinone, 2,5-dimethyl-p-quinone, 2,6-dimethoxy-p-quinone, tetrachloro-p-quinone, dichlorodicyano-p-quinone, duroquinone, rifamycin S, alkyl nitrites, hydrogen peroxide, alkali metal persulfates, alkali metal ferricyanides, cupric acetate, mercuric acetate and manganese dioxide.

5. A process as in claim 1 wherein the reaction between the rifamycin S derivative and the cysteine ester and the subsequent contacting of the obtained 3-(2-substituted ethylthio)-rifamycin SV derivative with an oxidizing agent are performed directly without isolating the intermediate.

6. A process as in claim 5 wherein the rifamycin S derivative and the cysteine ester are reacted in the presence of an oxidizing agent selected from the group consisting of rifamycin S, duroquinone, chloranyl and dichlorodicyano-p-quinone at a controlled pH between 4.2 and 4.8.

7. A process as in claim 1 for preparing rifamycin P wherein the thiazolorifamycin carboxy ester is decarboxylated by means of mild alkaline hydrolysis followed by acidification.

8. A process as in claim 1 for preparing rifamycin Q wherein the carboxy ester moiety of the thiazolorifamycin is reduced to hydroxymethyl by means of a reducing agent selected from the group consisting of NaAlH₄, LiAlH₄, AlH₃, LiAlH(OCH₃)₃, NaBH₄ excess, ((CH₃)₂CH—CH₂—)₂AlH, NaAl(OCH₂—CH₂OCH₃)₂H₂, NaB(OCH₃)₃H and CaCl₂/NaBH₄.

9. A process as in claim 1 wherein rifamycin P is prepared, comprising the further step of submitting said rifamycin P to alkaline hydrolysis to obtain the corresponding 25-deacetyl derivative.

10. The 25-deacetyl rifamycin P of the formula: